US010961164B2

(12) United States Patent
Schlueter

(10) Patent No.: US 10,961,164 B2
(45) Date of Patent: Mar. 30, 2021

(54) FACILITY AND PROCESS FOR THE RECYCLING OF BIOMATERIAL

(71) Applicant: Eisenmann SE, Boeblingen (DE)

(72) Inventor: Thomas Schlueter, Weil im Schoenbuch (DE)

(73) Assignee: EISENMANN SE, Böblingen (DE)

( * ) Notice: Subject to any disclaimer, the term of this patent is extended or adjusted under 35 U.S.C. 154(b) by 214 days.

(21) Appl. No.: 15/458,550

(22) Filed: Mar. 14, 2017

(65) Prior Publication Data

US 2017/0267598 A1    Sep. 21, 2017

(30) Foreign Application Priority Data

Mar. 16, 2016  (DE) .................... 10 2016 003 256.1

(51) Int. Cl.
| | |
|---|---|
| C05F 17/80 | (2020.01) |
| C12P 5/02 | (2006.01) |
| C05F 17/90 | (2020.01) |
| C12M 1/00 | (2006.01) |
| C12M 1/06 | (2006.01) |

(Continued)

(52) U.S. Cl.
CPC ............ C05F 17/80 (2020.01); C05F 17/964 (2020.01); C12M 21/04 (2013.01); C12M 23/58 (2013.01); C12M 27/06 (2013.01); C12M 29/00 (2013.01); C12M 47/16 (2013.01); C12M 47/20 (2013.01); C12P 5/023 (2013.01); Y02E 50/30 (2013.01); Y02P 20/145 (2015.11); Y02W 30/40 (2015.05)

(58) Field of Classification Search
None
See application file for complete search history.

(56) References Cited

U.S. PATENT DOCUMENTS

| | | | | |
|---|---|---|---|---|
| 4,252,901 A | * | 2/1981 | Fischer | ................ C12M 21/04 |
| | | | | 435/167 |
| 5,529,692 A | * | 6/1996 | Kubler | .................. C02F 3/006 |
| | | | | 210/603 |

(Continued)

FOREIGN PATENT DOCUMENTS

| | | |
|---|---|---|
| DE | 195 16 378 A1 | 10/1995 |
| DE | 196 12 010 A1 | 9/1997 |

(Continued)

*Primary Examiner* — Wayne A Langel
(74) *Attorney, Agent, or Firm* — Schroeder Intellectual Property Law Group, LLC

(57) ABSTRACT

A facility for the recycling of biomaterial with a fermentation stage, whereby the fermentation stage has a fermentation chamber for the production of biogas through anaerobic fermentation of the biomaterial, and with a hygiene stage that is positioned downstream from the fermentation stage, whereby the hygiene stage has a hygienization chamber for the reception and the thermal hygienization of biomaterial discharged from the fermentation stage. A process for the recycling of biomaterial by zymosis is also provided, whereby biogas is produced in a fermentation stage through anaerobic fermentation of the biomaterial, whereby the biomaterial is, after flowing through the fermentation stage, conveyed to a hygiene stage in which the biomaterial thermal is hygienized, and whereby the biomaterial is, after flowing through the hygiene stage, made available as recyclable agricultural, hygienized fermentation residue.

7 Claims, 3 Drawing Sheets

(51) Int. Cl.
*C12M 1/107* (2006.01)
*C05F 17/964* (2020.01)

(56) References Cited

U.S. PATENT DOCUMENTS

| | | | | |
|---|---|---|---|---|
| 6,454,944 | B1* | 9/2002 | Raven | C12M 21/04 210/180 |
| 6,492,135 | B1 | 12/2002 | Larsen | |
| 2004/0262220 | A1* | 12/2004 | Binnig | C02F 3/286 210/603 |
| 2005/0000906 | A1* | 1/2005 | Blais | A01C 3/00 210/704 |
| 2005/0155928 | A1* | 7/2005 | Jarventie | C12M 47/18 210/603 |
| 2007/0062231 | A1* | 3/2007 | Spindler | C05C 3/005 71/11 |
| 2007/0105205 | A1* | 5/2007 | Jarventie | C05C 3/00 435/161 |
| 2008/0193994 | A1* | 8/2008 | Choate | C12M 21/04 435/167 |
| 2009/0035834 | A1* | 2/2009 | Weidele | C12M 43/08 435/170 |
| 2009/0239209 | A1* | 9/2009 | Lutz | C05F 17/0027 435/3 |
| 2010/0173354 | A1* | 7/2010 | Schwarz | C12M 21/04 435/41 |
| 2011/0247378 | A1* | 10/2011 | Begley | C05C 1/00 71/8 |
| 2013/0065290 | A1* | 3/2013 | Mate | C02F 11/04 435/167 |
| 2013/0288326 | A1* | 10/2013 | Pullammanappallil | C12M 21/16 435/167 |
| 2014/0157777 | A1 | 6/2014 | Kramer et al. | |
| 2016/0107649 | A1 | 4/2016 | Takeuchi et al. | |
| 2016/0230134 | A1* | 8/2016 | Ludtke | C12P 5/023 |

FOREIGN PATENT DOCUMENTS

| | | |
|---|---|---|
| DE | 197 11 355 A1 | 9/1998 |
| DE | 600 14 634 T2 | 2/2006 |
| DE | 10 2007 034 642 A1 | 1/2009 |
| DE | 10 2011 015 611 A1 | 10/2012 |
| DE | 10 2013 012 289 A1 | 1/2015 |
| DE | 10 2013 213 258 A1 | 1/2015 |
| DE | 10 2013 021 526 A1 | 6/2015 |
| DE | 10 2014 010 641 A1 | 1/2016 |
| EP | 0 866 042 A2 | 9/1998 |
| EP | 2 821 475 A1 | 1/2015 |
| WO | 00/70014 A1 | 11/2000 |
| WO | 2015/001091 A1 | 1/2015 |

* cited by examiner

FACILITY AND PROCESS FOR THE RECYCLING OF BIOMATERIAL

RELATED APPLICATION

The present application claims priority to German Application No. 10 2016 003 256.1 filed Mar. 16, 2016—the contents of which are fully incorporated herein by reference.

FIELD OF THE INVENTION

The invention relates to a facility for the recycling of biomaterial with a fermentation stage, whereby the fermentation stage has a fermentation chamber for the production of biogas through anaerobic fermentation of the biomaterial.

The invention also relates to a process for the recycling of biomaterial through zymosis, whereby biogas is produced in a fermentation stage through anaerobic fermentation of the biomaterial.

BACKGROUND OF THE INVENTION

DE 195 16 378 A1 describes a process for the fermentation of organic residual materials with a thermophilic biogas reactor. Since the thermophilic fermentation of highly nitrogenous wastes is extremely difficult, dilution water and/or dilution substrate, which entail high technical and procedural expenditures, are accordingly generally used.

A process for the processing of biological wastes, in which biological wastes are shredded, mixed and, after the sieving out of impurities, subjected to hydrolysis, along with water in the form of a suspension, whereby a hygienization of the biological wastes is carried out after hydrolysis and before fermentation, is known from DE 197 11 355 A1. Furthermore, in accordance with DE 197 11 355 A1, a fermentation sludge remaining after the fermentation is dewatered and conveyed to composting. During composting, however, the lack of carbon and structural material, in particular, can lead to difficulties.

The disadvantages of the known process may, for example, be the relatively high expense for equipment or technical and procedural expenditures, as the case may be, as well as the relatively low level of recycling that is achieved during the processing of the biomaterial.

SUMMARY OF THE INVENTION

A task of the present invention is to provide a facility for the recycling of biomaterial, which makes possible a particularly economical recycling of biomaterial and improved process control relative to the state of the art.

This task may be solved by means of a facility of the type stated above, whereby the facility has a hygiene stage downstream from the fermentation stage, and whereby the hygiene stage has a hygienization chamber for the reception and thermal hygienization of biomaterial discharged from the fermentation stage. A reliable hygienization can thereby be guaranteed, even upon relatively low fermentation temperatures within a continuous process. An economically advantageous recycling and an efficient hygienization of biomaterial is made possible in accordance with the invention, even if the biomaterial is characterized by high impurities and inhomogeneity. A downstream separation of the fermentation residue into a fluid phase and a solid phase with subsequent hygienization, for example, can be omitted through the composting of the solid phase and the heating of the fluid phase.

It may be advantageous if the fermentation chamber is configured as a reactor with plug flow. A greater load-bearing capacity, as well as a low level of recirculation in the fermentation chamber, can thereby be brought about. Furthermore, positive effects are thereby brought about on the biodegradation level and the hygienizability of the biomaterial.

One particularly favorable technical solution is provided if the hygienization chamber is configured as a reactor with plug flow. A greater load-bearing capacity and a low recirculation can thereby be brought about in the hygiene stage, for example.

It may be suitable if the volume of the hygienization chamber is smaller than the volume of the fermentation chamber.

One configuration that is particularly favorable in regard to efficiency and process control is present if the fermentation chamber has a discharge device that is connected with a feeding device of the hygienization chamber.

A pumping device for conveying biomaterial from the discharge device of the fermentation chamber to the feeding device of the hygienization chamber can preferably be provided.

The hygiene stage can advantageously have at least two hygienization chambers. A continuous or quasi-continuous process control, as the case may be, can thereby be favored if, for example, the residence time of the biomaterial in the fermentation stage is longer than in the hygiene stage.

In order to improve the process control, it can, furthermore, be advantageous if the hygiene stage is designed in such a way that the at least two hygienization chambers can be operated in parallel.

Furthermore, it may be suitable if the fermentation stage and the hygiene stage are positioned in a common structure.

A task of the invention is also solved by a process of the type stated above, in which the biomaterial, after flowing through the fermentation stage, is conveyed to a hygiene stage in which the biomaterial thermal is hygienized, whereby the biomaterial, after flowing through the hygiene stage, is made available as recyclable agricultural fermentation residue. Significant advantages of the process appear in analogy to the advantages of the facility in accordance with the invention.

The fermentation of the biomaterial in the fermentation stage can preferably take place in a mesophilic temperature range. Biomaterial can thereby be reliably fermented with increased protein and/or nitrogen content, for example.

It may be suitable if the biomaterial resides in the fermentation stage for a longer time than in the hygiene stage or in the fermentation stage for the same time as in the hygiene stage.

The biomaterial can advantageously flow through the fermentation stage in a plug flow. A greater load-bearing capacity and a low recirculation in the fermentation stage can thereby be brought about. Furthermore, positive effects can arise in regard to the biodegradation level and the hygienizability of the biomaterial.

In one advantageous further development, the biomaterial can flow through the hygiene stage in a plug flow. A greater load-bearing capacity as well as a low recirculation in the hygiene stage can thereby be brought about and the efficiency of the hygienization can be increased.

The biomaterial can preferably be conveyed in the form of biological waste.

For example, in regard to a continuous or quasi-continuous process control, as the case may be, it may be advantageous if the biomaterial is, after flowing through the fermentation stage, divided into at least two partial currents that are conveyed to the hygiene stage.

Other advantages and aspects of the present invention will become apparent upon reading the following description of the drawings and detailed description of the invention.

BRIEF DESCRIPTION OF THE DRAWINGS

Additional advantageous configurations of the invention are evident from the following description. Exemplary embodiments of the invention are thereby illustrated in further detail by means of the diagrams without being restricted to these. The following are depicted in simplified, schematic depiction.

DETAILED DESCRIPTION OF THE PRESENT INVENTION

While this invention is susceptible to embodiments in many different forms, there is described in detail herein, preferred embodiments of the invention with the understanding that the present disclosures are to be considered as exemplifications of the principles of the invention and are not intended to limit the broad aspects of the invention to the embodiments illustrated.

Figure 1:
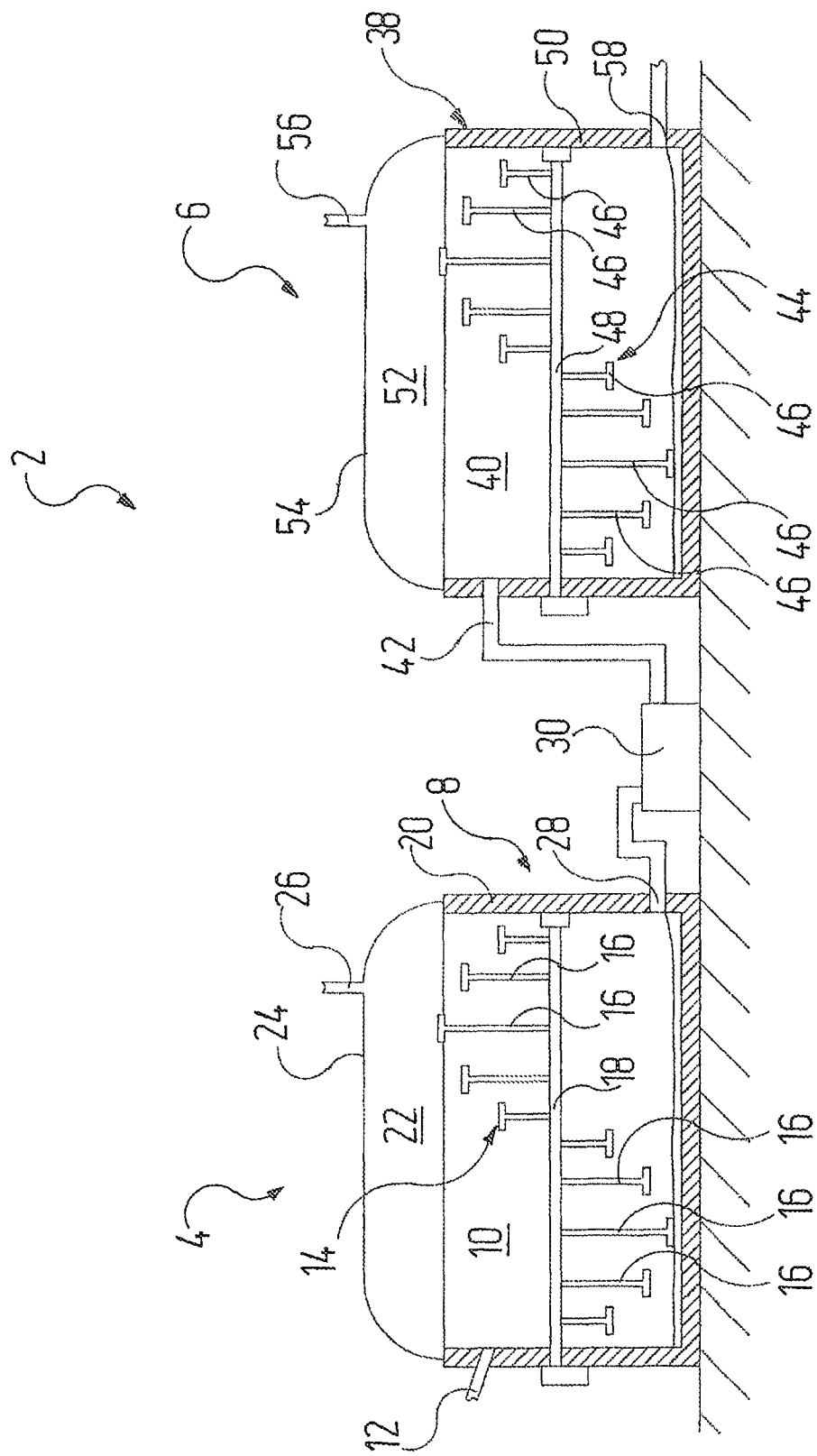
FIG. 1: A partial view of a facility for the recycling of biomaterial.

FIG. 1 depicts a part of a facility 2 for the recycling of biomaterial with a fermentation stage 4, and a hygiene stage 6.

The fermentation stage 4 is equipped with a container 8, which is also termed a fermentation container, and which has a fermentation chamber 10 for the production of biogas through anaerobic fermentation of the biomaterial. The container 8 of the fermentation stage 4 has a feeding device 12, which is configured to bring biomaterial into the fermentation chamber 10. Biomaterial, which is conveyed to the fermentation with the help of the feeding device 12, can, in particular, be biological waste, such as from the biological waste disposal of household and/or residual materials from the food industry or from agribusiness and/or market wastes, as the case may be.

Biogas recyclable as energy is recovered in the fermentation container, whereby the container 8 depicted as an example is positioned horizontally. In principle, fermentation containers of different geometrical configurations, which can be positioned horizontally or vertically, for example, can be used. Concrete and/or steel, particularly stainless steel, for example, can be used as materials for the production of a fermentation container. Vertical fermentation containers can, for example, be provided with a circular cross-section. Horizontal fermentation containers, for example, can have a rectangular or square cross-section. Horizontal fermentation containers, for example, can even be configured essentially cylindrically.

The container 8 of the fermentation stage 4 depicted schematically in FIG. 1 can, for example, be configured as a so-called plug flow fermenter, whereby the fermentation chamber 10 forms a reactor with a plug flow. The contents of the container 8 are, because of the displacement effect of the material that is brought in—similar to a plug—thereby transported horizontally through the fermentation chamber 10. The biomaterial passes through the fermentation chamber 10 in a plug flow. The fermentation chamber 10 configured as a reactor with plug flow can, for example, be loaded continuously or quasi-continuously with biomaterial.

An agitator 14 is provided in the fermentation chamber 10. The agitator 14 has an agitator shaft 18 on which stirring devices 16, which are only sometimes provided with reference figures, are positioned. A mixing of the fermenter contents by means of the stirring device 14 takes place, whereby the formation of floating and sinking layers is reduced and the microbiological activity in the fermenter is positively influenced. In the example depicted, the agitator 14 is configured as a reel stirring device, whereby the stirring devices 16 are placed along the agitator shaft 18 as agitator arms. In the example depicted, the stirring devices 16 project radially outwardly from the agitator shaft 18. It may be advantageous if the stirring devices 16 is positioned helically in at least one partial area of the container 8 and—as indicated in the diagram—are equipped on their ends with paddles. In the present exemplary embodiment, these paddles proceed in parallel to the agitator shaft 18.

The biogas that arises through the fermentation of the biomaterial in the container 8 of the fermentation stage 4 accumulates in a gas reservoir 22 underneath a cover 24. As indicated schematically in the example, the gas reservoir 22 is bounded at the top by the cover 24 and at the bottom by the level of the material located in the fermentation chamber 10. The cover 24 can, for example, be configured as a foil cover of flexible, gas-tight material. Another embodiment of the cover 24 is, for example, a so-called "membrane roof". In a membrane roof, an external membrane, below which a gas reservoir membrane is positioned and by which the gas reservoir is bounded at the top, is generally provided. Alternately or in addition to the positioning of the gas reservoir 22 depicted, it is also possible to provide a separate storage unit for gas storage. A separate storage unit can, for example, be an external foil gas storage unit.

By means of a gas sampling device 26 that is only indicated in the diagram, the biogas recovered in the fermentation container can be removed from the gas reservoir 22 and conveyed for use and/or additional processing and/or storage.

In the example depicted, a discharge device 28 for the fermented biomaterial is provided on the side of the casing 20 of the fermentation container positioned opposite the feeding device 12.

The facility for recycling biomaterial depicted in FIG. 1, particularly biological waste, is operated in such a way that the biomaterial, after flowing through the fermentation stage 4, is conveyed to a hygiene stage 6 downstream from the fermentation stage 4. The hygiene stage 6 is equipped with a container 38, in which the biomaterial conveyed to fermentation stage 4 is thermally hygienized.

In principle, the container 38 of the hygiene stage 6 can, in regard to its design, such as in regard to its structures, the materials used, and its positioning, for example, resemble the fermentation container described above. The container 38 of the hygiene stage 6 has a hygienization chamber 40, which is equipped with a feeding device 42 for biomaterial. In the example depicted, a discharge device 58 for the hygienized biomaterial is provided on the side of the casing 50 of this container 38 positioned opposite the feeding device 42.

The hygienization chamber 40 depicted schematically in FIG. 1 can preferably be configured as a reactor with plug flow. The contents of the container 38 are, because of the displacement effect of the material brought in—similar to a plug—thereby transported horizontally through the hygienization chamber 40. The biomaterial passes through the hygienization chamber 40 in a plug flow. The hygienization chamber 40 configured as a reactor with plug flow can, for example, be loaded with biomaterial continuously or quasi-continuously. Advantageously, steel can be used as the material for the formation of the hygienization chamber 40.

In the example depicted, the hygienization chamber 40 is, similarly to the fermentation chamber 10 described above, equipped with an agitator 44, which has an agitator shaft 48 on which stirring devices 46, which are only sometimes provided with reference figures, are positioned.

Biogas can also arise in the hygienization chamber 50. The biogas arising in the hygienization chamber 50 accumulates in a gas reservoir 52 underneath a cover 54, whereby the gas reservoir 52 and the cover 54 of the hygiene stage can, in principle, be constructed similarly to the gas reservoir 22 and the cover 24 of the fermentation stage 4. A gas sampling device 56 can also be provided in the hygiene stage, as indicated in the diagram. By means of a gas sampling device 56, biogas can be removed from the gas reservoir 52 of the hygiene stage 6 and conveyed to use and/or storage.

In accordance with the exemplary embodiment depicted, the discharge device 28 of the container 8 of the fermentation stage 4 is connected with the feeding device 42 of the container 38 of the hygiene stage 6 in order to convey biomaterial from the fermentation chamber 10 to the hygienization chamber 40. The biomaterial is thereby preferably pumped from the discharge device 28 of the fermentation stage 4 to the feeding device 42 of the hygiene stage 6 by means of a pumping device 30.

If both the fermentation chamber 10 and the hygienization chamber 40 operate in accordance with the principle of the plug flow, then it may be suitable, in particular, if the volume of the hygienization chamber 40 is smaller than the volume of the fermentation chamber 10.

Both the fermentation stage 4 and the hygiene stage 6 are designed for the recycling of biomaterial, such as biological waste, for example, with a high content of impurities and dry material.

The fermentation of the biomaterial, such as biological waste, for example, occurs in the fermentation stage 4 in the mesophilic temperature range, that is to say, at a comparatively low temperature, such as approx. 40° C., for example, or in a temperature range of approx. 37° C. to approx. 40° C., as the case may be.

In the hygiene stage 6, which is downstream from the fermentation stage 4, microorganisms are killed thermally, and the greatest possible degassing of the biomaterial takes place. Methane bacteria are killed at a hygienization temperature of approx. 60° and above. The methane emissions emanating from biomaterial that has flowed through the hygiene stage 6 can thereby be clearly reduced. A particularly secure interim storage is consequently made possible.

The hygiene stage 6 is, preferably, designed for operation at up to approx. 70° C. By that means, hygienically unobjectionable biomaterial is present on the discharge device 58 of the hygiene stage 6, which can be used in agriculture as a high-value fertilizer, for example. Regulation (EG) no. 1069/2009 and Regulation (EU) no. 142/2011 can thereby be complied with.

The fermentation container of the fermentation stage 4 is designed for the necessary residence time of the biomaterial or of the corresponding substrate, as the case may be, whereby the real minimum residence time in the fermentation stage 4, for example, can amount to approx. 14 hours. The container 38 of the hygiene stage 6 is designed for the residence time of the biomaterial that is necessary for the hygienization, whereby the real minimum residence time in the hygiene stage 6, for example, can amount to approx. 7 hours. It may be advantageous if the residence time of the biomaterial in the hygiene stage 6 is lower than the residence time in the fermentation stage 4. The process temperature in the hygiene stage 6 is clearly higher than the process temperature in the fermentation phase 4.

Figure 2:
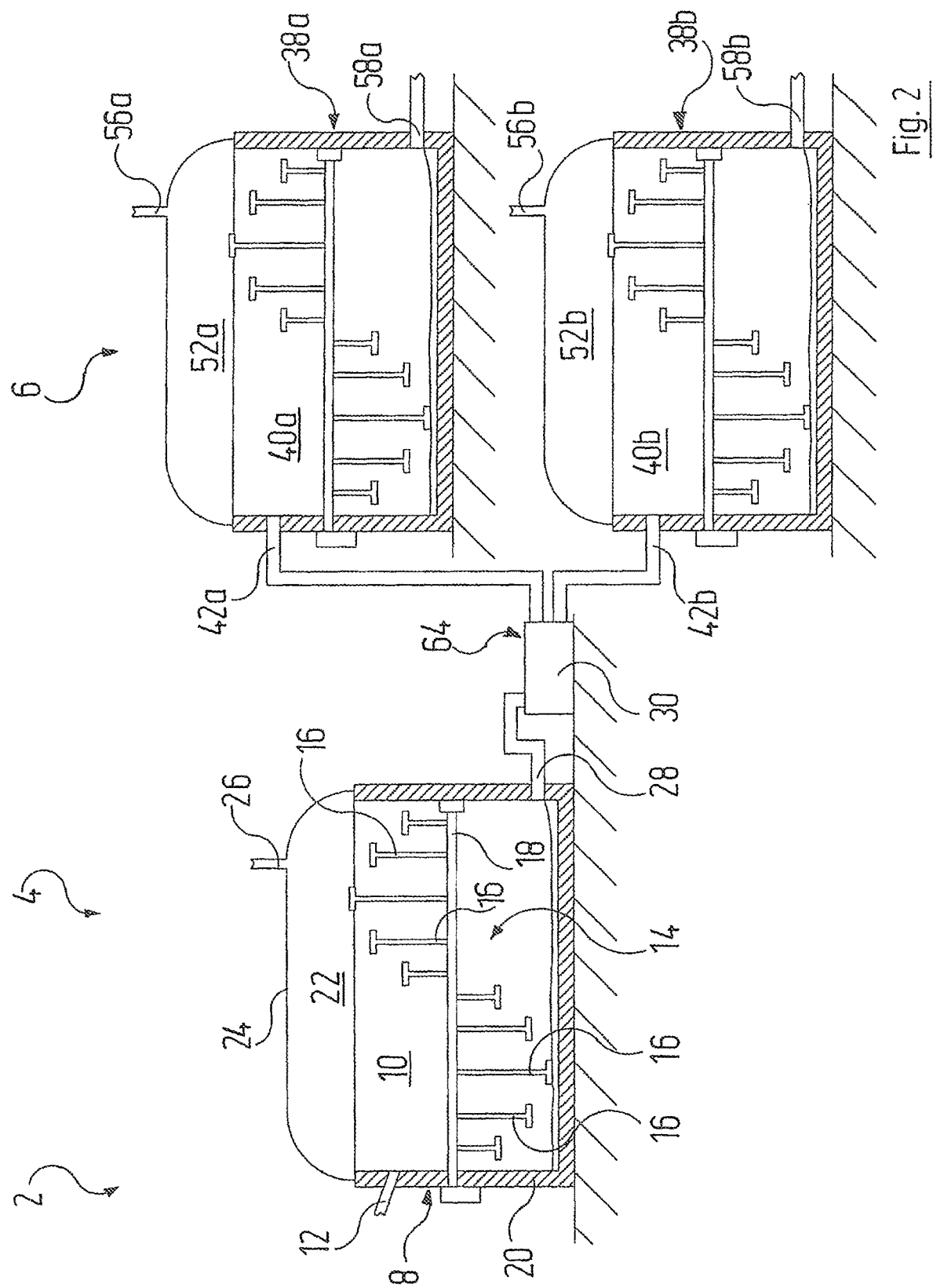
FIG. 2: A partial view of a facility for the recycling of biomaterial in an alternative configuration.

FIG. 2 depicts an additional example of a facility 2 for the recycling of biomaterial with a fermentation stage 4 and with a hygiene stage 6, whereby the fermentation stage 4 depicted here corresponds, in regard to its design, to fermentation stage 4 as described above in connection with FIG. 1.

The hygiene stage 6 in accordance with FIG. 2 is equipped with a first container 38-*a* and a second container 38-*b*. These containers 38-*a*, 38-*b* each have a hygienization chamber 40-*a* or 40-*b*, respectively, as well as a corresponding gas reservoir 52-*a* or 52-*b*, respectively. The gas reservoirs 52, 52-*b* each have a gas sampling device 56-*a* or 56-*b*, respectively. The hygienization chambers 40-*a*, 40-*b*, each have a feeding device 42-*a* or 42-*b*, respectively, for biomaterial. The discharge devices 58-*a* or 58-*b*, respectively, are provided for the hygienized biomaterial on the side of the container 38-*a*, 38-*b* positioned opposite the feeding devices 42-*a*, 42-*b*. Additional units of the container 38-*a*, 38-*b*, as well as of the hygienization chambers 40-*a*, 40-*b* and of the gas reservoir 52-*a*, 52-*b*, are, for the sake of greater clarity, not provided with reference figures in FIG. 2.

The first hygienization chamber 40-*a* and the second hygienization chamber 40-*b* of the hygiene stage 6 are positioned, in terms of process technology and in regard to the material flow of the biomaterial, next to one another. The two hygienization chambers 40-*a* and 40-*b* of the hygiene stage 6 are positioned downstream from the fermentation chamber 10 and downstream from the fermentation stage 4.

The discharge device 28 of the container 8 of the fermentation stage 4 is, in accordance with the example depicted in FIG. 2, connected both with the feeding device 42-*a* of the first container 38-*a* as well as with the feeding device 42-*b* of the second container 38-*b* of the hygiene stage 6. In order to convey biomaterial from the fermentation chamber 10 to the hygienization chambers 40-*a*, 40-*b*, a conveying device, which has a pumping device 30 in the example depicted, is provided.

The conveying device additionally has a separating device 64, which divides the current of the biomaterial coming from the fermentation chamber 10 into several partial currents. In the example depicted, a first partial current leads from the separating device 64 to the feeding device 42-*a* of the first container 38-*a* of the hygiene stage 6. A second partial current leads from the separating device 64 to the feeding device 42-*b* of the second container 38-*b* of the hygiene stage 6. Both hygienization chambers 40-*a*, 40-*b* are, in accordance with the exemplary embodiment depicted here, operated in parallel. The division of the biomaterial discharged from the fermentation chamber 10 to several hygienization chambers 40-*a*, 40-*b* can, for example, be advantageous precisely then if the facility 2 is preferably designed in such a way that the residence time of the biomaterial in the hygiene stage 6 ensures a reliable hygienization of the fermentation product. The configuration of the facility 2 depicted in FIG. 2 favors a continuous or quasi-continuous operation, as the case may be, of the fermentation stage 4 and of the hygiene stage 6.

Figure 3:
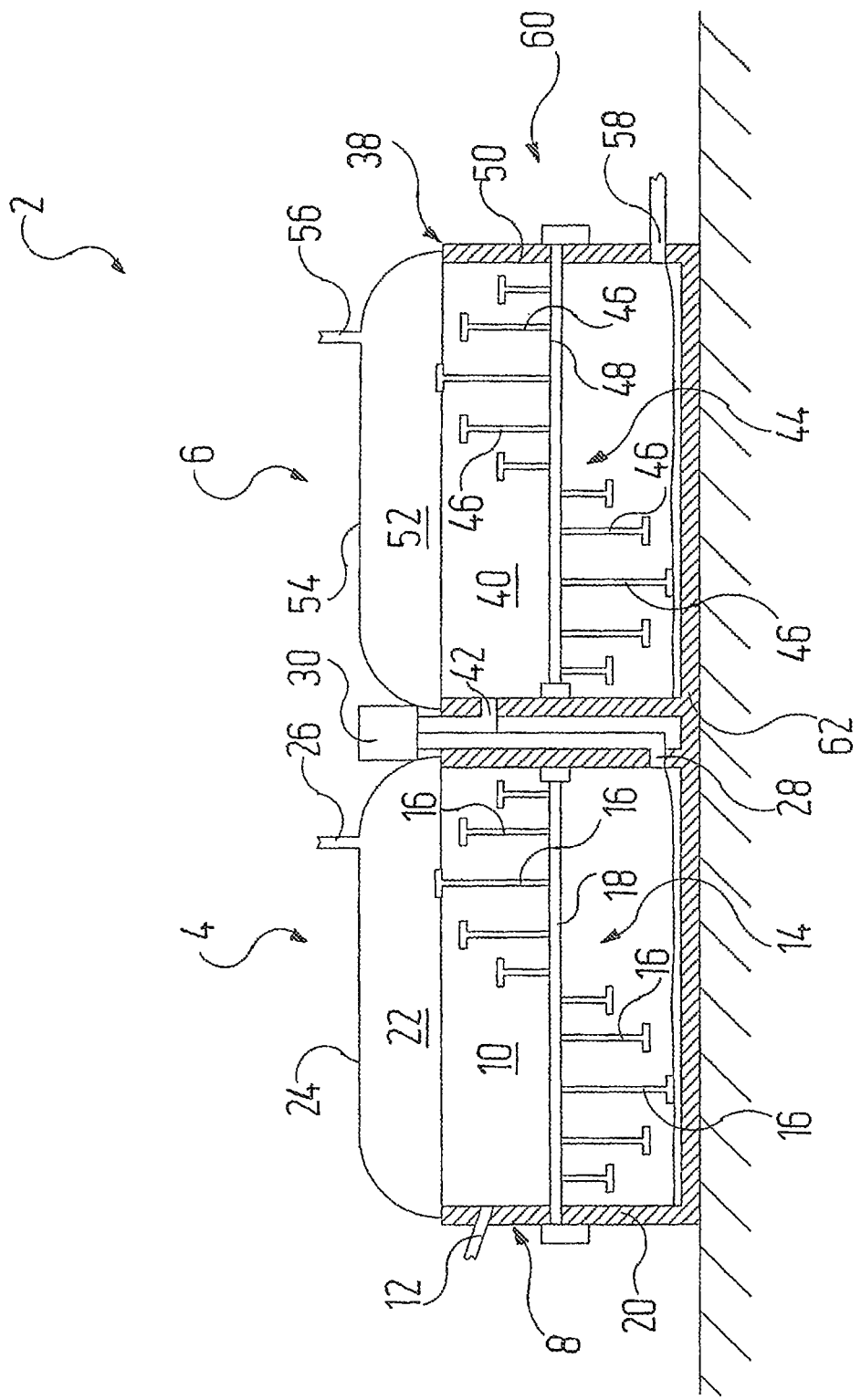
FIG. 3: A partial view of a facility for the recycling of biomaterial in an additional alternative configuration.

FIG. 3 also depicts a part of a facility 2 for the recycling of biomaterial with a fermentation stage 4 and a hygiene stage 6. The facility 2 depicted here by way of example differs from the example of the facility 2 depicted in FIG. 1 through the fact that the fermentation stage 4 and the hygiene stage 6 are, in accordance with FIG. 3, combined in their constructive design. The casing 20 of the container 8 of the fermentation stage 4 and the casing 50 of the container 38 of the hygiene stage 6, for example, can thereby have common elements, such as a common base plate 62, for example.

While the fermentation stage 4 and the hygiene stage 6 are, in accordance with FIG. 1, constructed as spatially separated structures, the fermentation stage 4 and the hygiene stage 6 can, in accordance with FIG. 3, also be alternately be constructed in a common structure.

One concept that forms the basis for the invention can be summarized as follows: The present invention relates to a facility 2 for the recycling of biomaterial, with a fermentation stage 4, whereby the fermentation stage 4 has a fermentation chamber 10 for the production of biogas through anaerobic fermentation of the biomaterial, and with a hygiene stage 6 that is positioned downstream from the fermentation stage 4, whereby the hygiene stage 6 has a hygienization chamber 40, 40-a, 40-b for the reception and the thermal hygienization of the biomaterial discharged from the fermentation stage 4. The invention also relates to a process for the recycling of biomaterial by means of zymosis, whereby biogas is produced, in a fermentation stage 4, through the anaerobic fermentation of the biomaterial, whereby the biomaterial is, after flowing through the fermentation stage 4, conveyed to a hygiene stage 6 in which the biomaterial thermal is hygienized, and whereby the biomaterial is, after flowing through the hygiene stage 6, made available as recyclable hygienized agricultural fermentation residue. By that means, biological wastes that are characterized by high impurities and inhomogeneity can also be fermented mesophilically and, after hygienization, be conveyed to an additional use, such as fertilizer, for example.

While in the foregoing there has been set forth various embodiments of the invention, it is to be understood that the present invention may be embodied in other specific forms without departing from the spirit or central characteristics thereof. The present embodiments, therefore, are to be considered in all respects as illustrative and not restrictive, and the invention is not to be limited to the details given herein. While specific embodiments have been illustrated and described, numerous modifications come to mind without significantly departing from the characteristics of the invention and the scope of protection is only limited by the scope of the accompanying claims.

I claim:

1. A process for the recycling of biomaterial through zymosis, comprising:
    feeding biomaterial to a fermentation stage;
    stirring the biomaterial in the fermentation stage with a first agitator;
    producing biogas in the fermentation stage by anaerobic fermentation of the biomaterial,
    conveying the biomaterial from the fermentation stage to a hygiene stage after flowing through the fermentation stage, wherein in the hygiene stage the biomaterial is thermally hygienized at a temperature of at least 60° C.,
    stirring the biomaterial in the hygiene stage with a second agitator, and
    making the biomaterial available as recyclable agricultural fermentation residue after flowing through the hygiene stage.

2. The process of claim 1, wherein the fermentation of the biomaterial in the fermentation stage takes place in a mesophilic temperature range.

3. The process of claim 1, wherein the biomaterial resides for a longer time in the fermentation stage than in the hygiene stage or for the same time in the fermentation stage as in the hygiene stage.

4. The process of claim 1, wherein the biomaterial passes through the fermentation stage in a plug flow.

5. The process of claim 1, wherein the biomaterial passes through the hygiene stage in a plug flow.

6. The process of claim 1, wherein the biomaterial is conveyed in the form of biological waste.

7. The process of claim 1, wherein the biomaterial is, after flowing through the fermentation stage, divided into at least two partial currents which are conveyed to the hygiene stage.

* * * * *